United States Patent [19]

Simmons

[11] Patent Number: 5,702,693
[45] Date of Patent: Dec. 30, 1997

[54] GYPSUM REMOVAL COMPOSITION AND METHOD OF REMOVING GYPSUM FROM SKIN

[75] Inventor: Donald L. Simmons, Pierrefonds, Canada

[73] Assignee: Draxis Health Inc., Mississauga, Canada

[21] Appl. No.: 568,510

[22] Filed: Dec. 7, 1995

[51] Int. Cl.$^6$ .................. A61K 7/025; A61K 7/035; A61K 31/74
[52] U.S. Cl. .................. 424/78.03; 424/63; 424/64; 424/69; 424/400; 514/844
[58] Field of Search .................. 424/63, 64, 69, 424/401, 78.03, 400; 514/844

[56] References Cited

U.S. PATENT DOCUMENTS

| | | | |
|---|---|---|---|
| 4,724,138 | 2/1988 | Duffy et al. | 424/63 |
| 4,879,107 | 11/1989 | Vanlerberghe et al. | 424/70 |
| 5,217,641 | 6/1993 | Herstein | 252/171 |
| 5,462,691 | 10/1995 | Shimada et al. | 252/174.17 |
| 5,510,107 | 4/1996 | Lecomte et al. | 424/401 |
| 5,518,647 | 5/1996 | Zocchi | 252/174.17 |
| 5,525,344 | 6/1996 | Wivell | 424/401 |

Primary Examiner—Thurman K. Page
Assistant Examiner—Kathryne E. Shellborne
Attorney, Agent, or Firm—Fitzpatrick, Cella, Harper & Scinto

[57] ABSTRACT

The present invention provides a method for removal of gypsum from the skin of a patient. The method comprising the steps of: (i) applying to the skin of a patient an aqueous liquid composition comprising a water-miscible organic solvent, an acid and an emollient, the aqueous liquid composition having a pH in the range of from about 2 to about 5; (ii) dissolving the gypsum in the aqueous liquid composition; and (iii) removing the aqueous liquid composition containing dissolved gypsum from the skin of the patient. An aspect of the invention also relates to a liquid composition, particularly one for removal of gypsum from the skin of a patient, the composition comprising water, a water-miscible organic solvent, an acid and an emollient, the liquid composition having a pH in the range of from about 2 to about 5, with the proviso that the acid is not salicylic acid. The method and composition are particularly well suited for removal of gypsum deposits from the skin of a patient after removal of a Plaster of Paris-based cast from the patient.

36 Claims, No Drawings

GYPSUM REMOVAL COMPOSITION AND METHOD OF REMOVING GYPSUM FROM SKIN

BACKGROUND OF THE INVENTION

1. Field of the Invention

The present invention relates to a gypsum removal composition and to a method for removing gypsum from skin.

2. Description of the Prior Art

In the art medicine it is known to facilitate healing of an injury, such as bone fractures, orthopaedic surgery and the like, by immobilization of an appropriate appendage or region of the patient. For decades, such immobilization was achieved by formation of a temporary cast over the appendage or region of the patient.

Initially, the conventional casts were based on Plaster of Paris. While advance in the art have resulted in the discovery of other cast materials (e.g. removable fibreglass casts and the like), casts based on Plaster of Paris are still used on a widespread basis. Indeed, in the art of podiatry, Plaster of Paris is used to prepare forms or molds from which therapeutic insoles and the like are produced.

As used throughout this specification, the terms "cast" is intended to have a broad meaning and encompasses, for example, casts used to facilitate healing of injuries and forms/molds used to produce prosthetic devices.

As is known in the art Plaster of Paris is derived from the mineral gypsum which is mined throughout North America. Chemically, gypsum is the dihydrate of calcium sulfate and may be represented by the following general formula:

$$CaSO_4.2H_2O$$

To produce cast materials, it is conventional to impregnate a fibrous matrix such as cloth, gauze and the like with a composition comprising Plaster of Paris. The impregnated fibrous matrix can be produced in a variety of forms such as splints or roll bandages.

In use, the impregnated fibrous matrix is dipped or immersed in water, excess water is allowed to drain from the fibrous matrix and the wetted fibrous matrix is then molded to the appendage or portion of the patient to be immobilized. Depending on the precise nature of the Plaster of Paris composition used to impregnate the fibrous matrix, the east will set in 2 to 8 minutes. Complete drying of the cast can take several hours to a week or more depending on the thickness of the cast, the precise nature of the Plaster of Paris composition used to impregnate the fibrous matrix, the ambient temperature and humidity level, and other factors.

When gypsum is heated at about 125° C., a portion of the water of crystallization is lost and Plaster of Paris is formed according to the following equilibrium reaction:

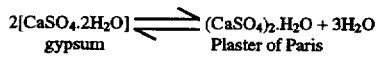

This reaction is reversible. Thus, when Plaster of Paris, impregnated in the fibrous matrix, is mixed with enough water to form a creamy paste, the reverse reaction occurs and the resulting crystals of gypsum interlace to form a rigid mass.

It is also known in the art to use various additives in the composition comprising Plaster of Paris used to impregnate the fibrous matrix.. Such additives include glue (retards rate of setting), colorants, deodorants and the like.

After the patient's injury has healed the cast may be removed by any suitable means. For example, the cast is broken and/or cut thereby facilitating removal from the patient. Once the cast has been removed it is known in the art that particulate gypsum will remain on the skin of the patient. Conventionally, attempts to remove this particulate gypsum involve repeating washings and/or scrubbings with soap and water. Unfortunately, such a protocol is ineffective for removing substantially all of the particulate gypsum from the skin of the patient. One of the reasons for this is that a significant portion of the particulate gypsum is situated in skin crevices and/or lines thereby exasperating attempts to remove the particulate gypsum. This is problematic since it is unsightly, uncomfortable and can give rise to skin irritation.

It would be desirable to have a method for removal of particulate gypsum from the skin of patient after removal of a cast. It would be also desirable to have a composition useful for removal of particulate gypsum from the skin of a patient after removal of a cast. It would be advantageous if the use of such a composition did not result in irritation of the skin of the patient and if one application of the composition could remove substantially all of the particulate gypsum on the skin of the patient.

SUMMARY OF THE INVENTION

It is an object of the invention to provide a novel method and composition for removal of gypsum from the skin of a patient which obviates or mitigates at least one of the foregoing disadvantages of the prior art.

Accordingly, in one of its aspects, the present invention provides a method for removal of gypsum from the skin of a patient comprising the steps of:

(i) applying to the skin of a patient an aqueous liquid composition comprising a water-miscible organic solvent, an acid and an emollient, the aqueous liquid composition having a pH in the range of from about 2 to about 5;

(ii) dissolving the gypsum in the aqueous liquid composition; and (iii) removing the aqueous liquid composition containing dissolved gypsum from the skin of the patient.

In another of its aspects, the present invention provides a liquid composition, particularly one for removal of gypsum from the skin of a patient, the composition comprising water, a water-miscible organic solvent, an acid and an emollient, the liquid composition having a pH in the range of from about 2 to about 5, with the proviso that the acid is not salicylic acid.

Thus, the Applicant has discovered that a topical liquid composition, uniquely formulated to dissolve gypsum and avoid skin irritation, is surprisingly and unexpectedly useful to remove particulate gypsum from the skin of a patient after removal of a cast based on Plaster of Paris. Further, topical liquid composition is formulated to dissolve organic resins, clues and/or binders which may be deposited on the skin of the patient from the cast. To the knowledge of the Applicant, such a uniquely formulated composition and the use thereof to remove particulate gypsum from the skin of a patient has been heretofore unknown.

DETAILED DESCRIPTION OF THE PREFERRED EMBODIMENTS

Thus, an aspect of the present invention relates to a method for removal of gypsum from the skin of a patient comprising the steps of:

(i) applying to the skin of a patient an aqueous liquid composition comprising a water-miscible organic solvent, an acid and an emollient, the aqueous liquid composition having a pH in the range of from about 2 to about 5;

(ii) dissolving the gypsum in the aqueous liquid composition; and (iii) removing the aqueous liquid composition containing dissolved gypsum from the skin of the patient.

Step (i) in the method comprises applying to the skin of a patient an aqueous liquid composition of particular composition. Of course, those of skill in the art will recognize that the aqueous liquid composition is applied to an area of the patient's skin which was previously covered by a Plaster of Paris based cast. The area of the patient's skin to the aqueous liquid composition is applied generally contains particulate gypsum deposited on the skin from the cast. This particulate gypsum may appear as a thin white film corresponding to the area of the skin previously covered by the cast. While larger particles of gypsum may be removed by rubbing the skin, optionally with water rinsing, a significant portion of the particulate gypsum is recalcitrant in its ability to be dislodged from the skin. It is this portion of the particulate gypsum to which the aqueous liquid composition is specifically targeted.

The aqueous liquid composition used in Step (i) of the present method comprises a water-miscible organic solvent, an acid and an emollient. The aqueous liquid composition is further characterized by having a pH in the range of from about 2.0 to about 5.0. At a pH level below about 2.0 the aqueous liquid composition becomes relatively corrosive resulting in an increased likelihood of the occurrence of skin irritation as a side effect. At a pH level above about 5.0, the aqueous liquid composition is so weakly acidic that it will be inefficient or ineffective in dissolving, and thereby facilitating removal of, gypsum from the skin of the patient. Preferably, the aqueous liquid composition has a pH in the range of from about 2.0 to about 4.0, more preferably from about 2.5 to about 3.5. The ideal pH is about 3.0.

The aqueous liquid composition used in Step (i) of the present method comprises an acid. Preferably, the acid is an organic acid. Preferably, the organic acid is a weak acid having a $pK_a$ value in the range of from about 1.0 to about 5.0, more preferably from about 2.5 to about 5.0, most preferably from about 3.0 to about 4.0. Non-limiting examples of suitable organic acids for use in the aqueous liquid composition in Step (i) of the present method may be selected from the group consisting of acetic acid, ascorbic acid, benzoic acid, citric acid, lactic acid, malic acid, malonic, acid, oxalic acid, salicylic acid, glycolic acid, tartaric acid and mixtures thereof. Preferably, the organic acid is selected from the group consisting of acetic acid, ascorbic acid, citric acid, lactic acid, malic acid, malonic acid, oxalic acid, glycolic acid and mixtures thereof. More preferably, the organic acid is selected from the group consisting of citric acid, lactic acid, malic acid and mixtures thereof. The most preferred organic acid is citric acid.

The acid present in the aqueous liquid composition used in Step (i) of the present method may also be an inorganic acid such as hydrochloric acid, hydrobromic acid, phosphoric acid, sulfuric acid and the like. Generally, these strong acids must be used in very dilute form since they are very corrosive and could give rise to skin irritation. For example, aqueous hydrochloric acid could be used in the aqueous liquid composition. The amount of aqueous hydrochloric acid required at various normalities and pH levels can be determined according to Table 1. Of course, those of skill in the art will readily be able to calculate the amounts of other strong, inorganic acids required to produce a pH value in the range of from about 2.0 to about 5.0. Of course, as will be apparent to those of skill in the art, the amount of strong, inorganic acid may be increased to ensure dissolution of the particulate gypsum on the skin of the patient provided that the acid is buffered such that it has a pH in the range of from about 2.0 to about 5.0. The choice and amount of buffering agent used (if present) is within the purview of a person skilled in the art.

TABLE 1

| Normality | Amount of Acid (Wt. %) | pH |
|---|---|---|
| 0.010000 | 0.03650000 | 2.00 |
| 0.007500 | 0.02737500 | 2.12 |
| 0.005000 | 0.01825000 | 2.30 |
| 0.002500 | 0.00912500 | 2.60 |
| 0.001000 | 0.00365000 | 3.00 |
| 0.000750 | 0.90273750 | 3.12 |
| 0.000500 | 0.00182500 | 3.30 |
| 0.000250 | 0.00091250 | 3.60 |
| 0.000100 | 0.00036500 | 4.00 |
| 0.000075 | 0.00027375 | 4.12 |
| 0.000050 | 0.00018250 | 4.30 |
| 0.000025 | 0.00009125 | 4.60 |
| 0.000010 | 0.00003650 | 5.00 |

As between organic acids and inorganic acids, it is preferred to utilize organic acids as these tend to mitigate the risk of skin irritation compared to inorganic acids. Further, inorganic acids are relatively toxic to handle and use.

Generally, the acid is Used in an mount to ensure a significant stoichiometric excess relative to the amount of particulate gypsum being removed from the skin of the patient. In the case of organic acids, for all practical purposes, the amount of acid used preferably is in the range of from about 2.0 to about 5.0, more preferably in the range of from about 2.0 to about 4.0, most preferably in the range of from about 2.0 to about 3.0, percent by weight of the aqueous liquid composition.

The most preferred acid (organic or inorganic) suitable for use in the aqueous liquid composition used in Step (i) of the present method is citric acid. Ideally, citric acid is used in an mount in the range of from about 2.0 to about 2.5 percent by weight of the aqueous liquid composition.

The liquid composition used in Step (i) of the present method is aqueous (i.e. it contains water at some level) and contains a water-miscible organic solvent. While the precise nature of the water-miscible organic solvent is not critical, it is preferred that the water-miscible organic solvent be selected from the group consisting of $C_1-C_{10}$ alcohols. Alternatively, the water-miscible organic solvent may be a ketone such as acetone. More preferably, the alcohol is selected from the group consisting of ethanol, isopropyl alcohol and mixtures thereof. Most preferably, the water-miscible organic solvent is isopropyl alcohol. Of course, those of skill in the art will recognize that it is desirable to utilize a water-miscible organic solvent which can be safely applied to the skin of a patient without any significant side effects and which does not have a significant drying effect when applied to skin.

While the relative mounts of water and water-miscible organic solvent used in the aqueous liquid composition are not particularly restricted, it is preferred that amounts be chosen to ensure dissolution of the other components of the aqueous liquid composition, namely the acid and the emollient. Practically, it is preferred that the aqueous liquid composition comprises a water:water-miscible organic solvent weight ratio in the range of from about 80:20 to about 20:80, more preferably in the range of from about 70:30 to about 30:70, even more preferably in the range of from about 60:40 to about 40:60, most preferably in the range of from about 55:45 to about 45:55.

The aqueous liquid composition used in Step (i) of the present method additionally comprises an emollient, preferably a skin emollient. As is known to those of skill in the arts of cosmetics and dermatology, an emollient is a substance that has a soothing, softening and/or lubricating effect when applied to the skin and results in the skin becoming more pliable through penetration of the emollient into the surface layers of the skin. An emollient also has a moisturizing effect on dry skin, preventing loss of water from the skin surface by forming an oily film. This is important in the context of the present method since the water-miscible organic solvent tends to have a de-moisturizing or drying effect on the skin. Generally, the emollient suitable for use in the aqueous liquid composition is a bland substance which can be one or more of a fat, a wax and an oil substance capable of being readily dissolved in the water/water-miscible organic solvent system.

Non-limited examples of emollients suitable for use in the aqueous liquid composition used in Step (i) of the present method may be selected from the group consisting of glycols (e.g. glycerin, propylene glycol, sorbitol, polyethylene glycol and the like), lipids (e.g. cholesterol, fatty acids, lecithin and the like), fatty acid esters (e.g. isopropyl palmitate, isopropyl myristate, dioctyl malate and the like), silicones (e.g. dimethicone and the like), waxes (e.g. carnauba wax, cocoa butter, beeswax, petrolam and the like), glycerides (e.g. glyceryl monostearate, glyceryl distearate and the like), vegetable oils (e.g. sesame oil, coconut oil, cottonseed oil, peppermint oil, castor oil, corn oil, safflower oil, soybean oil, canola oil, wheat germ oil and the like), water soluble moisturizing agents (e.g. urea, ureic acid and the like), fatty alcohols (e.g. cetyl alcohol, stearyl alcohol, cetostearyl alcohol and the like), mineral oil, lanolin derivatives, animal extracts (e.g. shark liver oil, cod liver oil and the like) and mixtures thereof.

The preferred emollient suitable for use in the aqueous liquid composition used in Step (i) of the present method may be selected from the group consisting of fatty acid esters.

The amount of emollient used in the aqueous liquid composition is not particularly restricted. Preferably the emollient is present in an amount in the range of from about 0.1 to about 10, more preferably from about 0.5 to about 5, most preferably from about 0.5 to about 2, percent by weight of the aqueous liquid composition.

Step (i) of the present method comprises applying to the skin of a patient the aqueous liquid composition described hereinabove. The method of topical application is not particularly restricted. Thus, the aqueous liquid composition may be applied with an absorbent device such as a swab, a wipe, a sponge and the like. Alternatively, the aqueous liquid composition may be atomized and applied as a spray to the skin. The spray may be aerosol or non-aerosol based.

Step (ii) of the present method comprises dissolving gypsum on the skin of the patient in the aqueous liquid composition. Generally, this will occur immediately upon contact of the aqueous liquid composition with the gypsum on the skin.

Step (iii) of the present method comprises removing the aqueous liquid composition containing dissolved gypsum from the skin of the patient. The manner of accomplishing this is not particularly restricted. When using the preferred embodiment of the aqueous liquid composition, it has been observed that Steps (i), (ii) and (iii) can occur concurrently when the composition is rubbed on the skin of the patient with an absorbent device. Alternatively, if the composition is sprayed on to the skin of the patient, Step (iii) may be accomplished by wiping the composition (now containing dissolved gypsum) off the skin with a suitable absorbent device as described hereinabove. Yet another contemplated alternative is to rinse the aqueous liquid composition off the skin of the patient after it has been sprayed thereon to dissolve the gypsum.

Once the Step (iii) has been conducted, the gypsum on the skin is substantially completely removed therefrom. Thus, to the naked eye, no gypsum is seen on the skin. This is a vast improvement from when the cast is originally removed from the patient.

Further, an advantageous feature of the present method is that the gypsum on the skin may be substantially completely removed therefrom using a single application of the aqueous liquid composition. While this an advantage of the present method, it is still with the scope and spirit of the invention to use repeated applications of a more dilute variant of the aqueous liquid composition.

As described hereinabove, an aspect of the present invention relates to a liquid composition, particularly one for removal of gypsum from the skin of a patient, the composition comprising water, a water-miscible organic solvent, an acid and an emollient, the liquid composition having a pH in the range of from about 2 to about 5, with the proviso that the acid is not salicylic acid. Further, the present liquid composition may be used advantageously as a skin conditioner applied prior to the application of a cast.

The discussion hereinabove concerning the preferred embodiments of the aqueous liquid composition for use in the present method apply equally to the aspect of the invention relating to the liquid composition (of course with the exception that the aspect of the invention relating to the liquid composition, the acid is not salicylic acid).

It will be readily understood by those of skill in the art that the liquid composition relating to the present invention may further comprise one or more additives conventionally used in the arts of cosmetics and dermatology. Thus, the liquid composition may further comprise one or more of viscosity enhancing agents (e.g. hydroxypropyl cellulose), buffering agents, colorants, fragrances, deodorants and the like. The choice and mount used of such additives is clearly within the purview of a person skilled in the art.

Embodiments of the invention will be described with reference to the following Examples which are not intended and should not be used to limit the scope of the invention.

EXAMPLES 1–12

In these Examples, a test Plaster of Paris cast was applied to the finger of a patient using the following protocol.

Orthoflex™ elastic plaster rolls (Johnson & Johnson Orthopaedics) were obtained and cut to produce a sample piece having the dimensions: 2"×¾". The sample piece was soaked in warm water (30° C.±2° C.) for approximately 1 minute. The soaked sample piece was molded to a ¾" band surrounding the finger of the patient and allowing to dry at room temperature for approximately 3 to 4 hours. After the cast was dry, it was removing from the finger by cutting with scissors.

In each case, a white band of particulate gypsum was observed on the finger of the patient corresponding to where the cast had been applied.

The white band of particulate gypsum was treated with various aqueous liquid compositions to assess the ability of the liquid compositions to remove the particulate gypsum. The formulation of each of the aqueous liquid compositions used in these Examples is provided in Table 2 (the amounts reported are in percent by weight), together with an indication of the performance of each composition in its ability to remove the particulate gypsum.

The aqueous liquid compositions were prepared by mixing the isopropyl alcohol and dioctyl malate for a period of at least 30 minutes. The acid (if present) and water were independently mixed with stirring until a solution was obtained. This solution was added to the isopropyl alcohol/dioctyl malate mixture and mixed with stirring for a period of approximately 30 minutes.

As will be apparent to those of skill in the art, Example 11 contained no acid and Example 12 consisted solely of water, and thus these Examples are provided for comparison purposes only.

The various aqueous liquid compositions were tested for their ability to remove particulate gypsum from the skin of the patient according to the following protocol. Fifteen (15) drops of the aqueous liquid composition was placed on a cotton ball which was then used to clean the finger gently. After solvent evaporation, the finger of the patient was checked for visible presence of particulate gypsum on the skin. The results were scored according to the following legend:

Good: No particulate gypsum visible on skin after treatment with aqueous liquid composition.

Marginal: Significant amount of particulate gypsum visible on skin removed with aqueous liquid composition leaving minor residual amount on skin.

Ineffective: Significant amount of particulate gypsum visible on skin after treatment with aqueous liquid composition (little or no particulate gypsum removed from skin).

With reference to Table 2, it will be apparent to those of skill in the art that the aqueous liquid compositions used in Examples 1–7 were particularly effective (a single treatment using minimal amount of aqueous liquid composition) in removing particulate gypsum from the skin of the patient. Further, it will be apparent to those of skill in the art that the aqueous liquid compositions used in Examples 8–10 were somewhat effective in removing particulate gypsum from the skin of the patient. It is contemplated that the use of a greater volume of and/or a repeat treatment with the aqueous liquid composition would improve the results obtained. Still further, aqueous liquid compositions which did not contain acid (Example 11) or which were based exclusively on water were ineffective in removing particulate gypsum from the skin of the patient.

While the invention has been described with reference to various preferred embodiments, including the foregoing Examples, it will be appreciated by those of skill in the art that numerous variations and modifications of these preferred embodiments are possible without departing from the spirit and scope of the invention.

TABLE 2

| Example | Water | Isopropyl Alcohol | Dioctyl Malate[1] | Acid | Acid Amount | Results |
|---|---|---|---|---|---|---|
| 1 | 40.0 | 56.0 | 2.0 | Malic | 2.0 | Good |
| 2 | 40.0 | 56.0 | 2.0 | Ascorbic | 2.0 | Good |

TABLE 2-continued

| Example | Water | Isopropyl Alcohol | Dioctyl Malate[1] | Acid | Acid Amount | Results |
|---|---|---|---|---|---|---|
| 3 | 40.0 | 56.0 | 2.0 | Acetic | 2.0 | Good |
| 4 | — | — | — | Salicylic[2] | 2.2 | Good |
| 5 | 40.2 | 56.0 | 2.0 | Citric | 1.7 | Good |
| 6 | 40.0 | 56.0 | 2.0 | Citric | 2.0 | Good |
| 7[3] | 40.2 | 56.0 | 2.0 | Citric | 1.7 | Good |
| 8 | 40.5 | 56.0 | 2.0 | Citric | 1.5 | Marginal |
| 9 | 40.7 | 56.0 | 2.0 | Citric | 1.3 | Marginal |
| 10 | 41.0 | 56.0 | 2.0 | Citric | 1.0 | Marginal |
| 11 | 42.0 | 56.0 | 2.0 | none | — | Ineffective |
| 12 | 100.0 | — | — | none | — | Ineffective |

[1]Emollient
[2]Kerasal ™ solution (commercially available from Spirig (Switzerland))
[3]Repeat test of liquid composition used in Example 5

What is claimed is:

1. A method for removal of gypsum from the gypsum skin of patient comprising the steps of:
   (i) applying to the skin of a patient an aqueous liquid composition consisting essentially of a water-miscible organic solvent, from about 1.7 to about 5.0 percent by weight of an organic acid having a $pK_a$ in the range of from about 1.0 to about 5.0 and from about 0.5 to about 5.0 percent by weight of an emollient, the liquid composition having a pH in the range of from about 2.0 to about 5.0,
   (ii) dissolving the gypsum in the aqueous liquid composition; and
   (iii) removing the aqueous liquid composition containing dissolved gypsum from the skin of the patient.

2. The method defined in claim 1, wherein the organic acid is present in an amount in the range of from about 2.0 to about 5.0 percent by weight of the aqueous liquid composition.

3. The method defined in claim 1, wherein the organic acid is present in an amount in the range of from about 2.0 to about 4.0 percent by weight of the aqueous liquid composition.

4. The method defined in claim 1, wherein the organic acid is present in an amount in the range of from about 2.0 to about 3.0 percent by weight of the aqueous liquid composition.

5. The method defined in claim 1, wherein the organic acid has a $pK_a$ value in the range of from about 2.5 to about 5.0.

6. The method defined in claim 1, wherein the organic acid has a $pK_a$ value in the range of from about 3.0 to about 4.0.

7. The method defined in claim 1, wherein the aqueous liquid composition has a pH in the range of from about 2.0 to about 4.0.

8. The method defined in claim 1, wherein the aqueous liquid composition has a pH in the range of from about 2.5 to about 3.5.

9. The method defined in claim 1, wherein the organic acid is selected from the group consisting of acetic acid, ascorbic acid, benzoic acid, citric acid, lactic acid, malic acid, malonic acid, oxalic acid, salicylic acid, glycolic acid, tartaric acid and mixtures thereof.

10. The method defined in claim 1, wherein the organic acid is selected from the group consisting of citric acid, lactic acid, malic acid and mixtures thereof.

11. The method defined in claim 1, wherein the acid is citric acid.

12. The method defined in claim 11, wherein the citric acid is present in an amount in the range of from about 2.0 to about 2.5 percent by weight of the aqueous liquid composition.

13. The method defined in claim 1, wherein the aqueous liquid composition comprises a water:water-miscible organic solvent weight ratio of from about 60:40 to about 40:60.

14. The method defined in claim 1, wherein the aqueous liquid composition comprises a water:water-miscible organic solvent weight ratio of from about 55:45 to about 45:55.

15. The method defined in claim 1, wherein the water-miscible organic solvent is selected from the group consisting of ethanol, isopropyl alcohol and mixtures thereof.

16. The method defined in claim 1, wherein the emollient is present in an amount of from about 0.5 to about 2 weight percent of the aqueous liquid composition.

17. The method defined in claim 1, wherein the emollient is selected from the group consisting of glycols, lipids, fatty acid esters, silicones, waxes, glycerides, vegetable oils, water soluble moisturizing agents, fatty alcohols, mineral oil, lanolin derivatives, animal extracts and mixtures thereof.

18. The method defined in claim 1, wherein the emollient is a fatty acid ester.

19. A liquid composition for removal of gypsum from the gypsum skin of a patient, the composition consisting essentially of water, a water-miscible organic solvent, from about 1.7 to about 5.0 percent by weight of an organic acid having a $pK_a$ in the range of from about 1.0 to about 5.0 and from about 0.5 to about 5.0 percent by weight of an emollient, the liquid composition having a pH in the range of from about 2.0 to about 5.0, with the proviso that the acid is not salicylic acid.

20. The liquid composition defined in claim 19, wherein the organic acid is present in an amount in the range of from about 2.0 to about 5.0 percent by weight of the aqueous liquid composition.

21. The liquid composition defined in claim 19, wherein the organic acid is present in an amount in the range of from about 2.0 to about 4.0 percent by weight of the aqueous liquid composition.

22. The liquid composition defined in claim 19, wherein the organic acid is present in an amount in the range of from about 2.0 to about 3.0 percent by weight of the aqueous liquid composition.

23. The liquid composition defined in claim 19, wherein the organic acid has a $pK_a$ value in the range of from about 2.5 to about 5.0.

24. The liquid composition defined in claim 19, wherein the organic acid has a $pK_a$ value in the range of from about 3.0 to about 4.0.

25. The liquid composition defined in claim 19, wherein the aqueous liquid composition has a pH in the range of from about 2.0 to about 4.0.

26. The liquid composition defined in claim 19, wherein the aqueous liquid composition has a pH in the range of from about 2.5 to about 3.5.

27. The liquid composition defined in claim 19, wherein the organic acid is selected from the group consisting of acetic acid, ascorbic acid, benzoic acid, citric acid, lactic acid, malic acid, malonic acid, oxalic acid, glycolic acid, tartaric acid and mixtures thereof.

28. The liquid composition defined in claim 19, wherein the organic acid is selected from the group consisting of citric acid, lactic acid, malic acid and mixtures thereof.

29. The liquid composition defined in claim 19, wherein the acid is citric acid.

30. The liquid composition defined in claim 29, wherein the citric acid is present in an amount in the range of from about 2.0 to about 2.5 percent by weight of the aqueous liquid composition.

31. The liquid composition defined in claim 19, wherein the liquid composition comprises a water:water-miscible organic solvent weight ratio of from about 60:40 to about 40:60.

32. The liquid composition defined in claim 19, wherein the liquid composition comprises a water:water-miscible organic solvent weight ratio of from about 55:45 to about 45:55.

33. The liquid composition defined in claim 19, wherein the water-miscible organic solvent is selected from the group consisting of ethanol, isopropyl alcohol and mixtures thereof.

34. The liquid composition defined in claim 19, wherein the emollient is selected from the group consisting of glycols, lipids, fatty acid esters, silicones, waxes, glycerides, vegetable oils, water soluble moisturizing agents, fatty alcohols, mineral oil, lanolin derivatives, animal extracts and mixtures thereof.

35. The liquid composition defined in claim 19, wherein the emollient is a fatty acid ester.

36. The liquid composition defined in claim 19, wherein the emollient is present in an amount in the range of from about 0.5 to about 2 percent by weight of the liquid composition.

* * * * *